(12) United States Patent
Nakajo et al.

(10) Patent No.: US 6,344,231 B1
(45) Date of Patent: Feb. 5, 2002

(54) YEAST EXTRACT COMPOSITION, YEAST FOR OBTAINING THE SAME, AND PROCESS FOR PRODUCING YEAST EXTRACT COMPOSITION

(75) Inventors: Yukihiro Nakajo, Shizuoka; Hiroyuki Sano, Miyazaki, both of (JP)

(73) Assignee: Nihon Tobacco Inc., Tokyo (JP)

( * ) Notice: Subject to any disclaimer, the term of this patent is extended or adjusted under 35 U.S.C. 154(b) by 0 days.

(21) Appl. No.: 09/509,481

(22) PCT Filed: Mar. 27, 1998

(86) PCT No.: PCT/JP98/01377

§ 371 Date: May 9, 2000

§ 102(e) Date: May 9, 2000

(87) PCT Pub. No.: WO99/16860

PCT Pub. Date: Apr. 8, 1999

(30) Foreign Application Priority Data

Sep. 29, 1997 (JP) .............................................. 9-263377

(51) Int. Cl.⁷ .............................. A23L 1/28; A23L 1/18; C12N 1/16
(52) U.S. Cl. ...................... 426/655; 426/656; 435/255.4
(58) Field of Search ................................ 435/91.3, 110, 435/116, 157, 255.4; 426/62, 60, 656, 655

(56) References Cited

U.S. PATENT DOCUMENTS 3,713,984 A * 1/1973 Bunting et al. ................ 195/82

FOREIGN PATENT DOCUMENTS

| JP | 459216 | 4/1970 |
|----|--------|--------|
| JP | 4821507 | 6/1973 |
| JP | 62201595 | 9/1987 |
| JP | 1265866 | 10/1989 |
| JP | 2793871 | 10/1995 |
| JP | 10-327802 | * 12/1998 |

* cited by examiner

*Primary Examiner*—Keith Hendricks
(74) *Attorney, Agent, or Firm*—Birch, Stewart, Kolasch & Birch, LLP

(57) ABSTRACT

A composition of yeast extract from genus Candida is provided. In the said composition, contents of mannitol, glutamic acid, alanine, 5'-IMP and 5'-GMP are above 0.5%, above 2.0%, above 0.5%, above 1.5% and above 1.5%, respectively, all of which should simultaneously be satisfied the condition. Increased contents of alanine and 5'-IG of the extract of Candida yeast resulted to obtain yeast extract having sea tangle (kombu) (Laminariales, kelps)-like taste and flavor.

12 Claims, No Drawings

YEAST EXTRACT COMPOSITION, YEAST FOR OBTAINING THE SAME, AND PROCESS FOR PRODUCING YEAST EXTRACT COMPOSITION

This application is the national phase under 35 U.S.C. §371 of PCT International Application No. PCT/JP98/01377 which has an International filing date of Mar. 27, 1998, which designated the United States of America.

TITLE OF THE INVENTION

A composition of yeast extract and yeast for obtaining the same, and a process for production of the composition of yeast extract.

FIELD OF THE INVENTION

This invention relates to a composition of yeast extract having taste, of kombu (Laminariales, kelps) and mushrooms and flavor thereof, new yeast strain for obtaining the same, and a process for production of the composition of yeast extract.

PRIOR ARTS AND PROBLEMS TO BE SOLVED BY THE INVENTION

Conventionally used extracts of mushrooms and kombu (Laminariales, kelps, hereinafter designated as kombu) have good flavors, but addition of these natural extracts to the foods can only show simple taste. In order to increase richness in flavor, heaviness of the taste and better taste, various seasonings have simultaneously to be added. Consequently, the said extracts are not satisfactory for the purpose of commonly used or all-purpose seasonings.

Recently, the use of natural seasonings is being recognized once again according to the natural food-oriented minds of the general consumers. For expanding applicable fields of natural seasonings, yeast extracts have widely been used, and demands for higher level of quality of the yeast extracts are increasing.

Generally, raw materials of yeast extracts include genus Saccharomyces such as baker's yeast and brewery yeast. The yeast extracts from Saccharomyces yeast have a specific yeast flavor. The yeast flavor is preferable for increasing meat taste, but is disadvantageous for taste of Japanese style cuisine.

The yeast extracts from genus Candida (hereinafter designated as Candida yeast extracts) have almost no yeast flavor which is specific to yeast extracts originated from yeast belonging to genus Saccharomyces. Furthermore, Candida extract can be used in all-purpose seasonings preferable to the taste of Japanese cuisine having savory (umami) by using nucleic acids which are rich in Candida yeast. (Japanese Patent Unexamined Publication No. 62-201595), Japanese Patent Examined Publications No. 7-93871 and No. 56-46824).

These prior technologies have objective to increase the taste of nucleic acids. For this purpose, the yeast is treated in order to increase the content of nucleic acids by enzymatic decomposition. Consequently, the content of free amino acids is relatively low and this gives simple taste and flavor.

In order to improve this disadvantage, the invention of Japanese Pat. Unexam. Publ. No. 9-294581 discloses an increased intracellular glutamic acid content by obtaining yeast belonging to genus Saccharomyces which is resistant to glutamic acid antagonist. The yeast extract of the invention is, however, not able to improve flavor due to removing Saccharomyces yeast flavor.

For masking undesirable yeast flavor of the yeast extracts and adding specific good flavor to foods and cooking, a method is conventionally practiced which adds flavors such as dried bonito flavor and smoke flavor, other than yeast extract whose origin is not yeast extracts. This method is, however, complicated due to processing and causes higher production cost. Consequently, it is preferable for the yeast itself to have a specific good flavor in yeast. No trials have been made to add or to generate specific good flavor and taste in the composition of Candida yeast extract per se.

Furthermore, a method for preparing sea tangle (kombu)-like taste using sugar alcohol, potassium and glutamic acid is known (Japanese Pat. Exam. Publ. No. 6-75479 and ibid. 7-114646). This method is only a combination of chemical compounds for preparing a taste composition, and the resulting seasonings are different from the natural flavor. Therefore, the method can not provide a seasoning with a natural complex flavor. Consequently, in order to prepare sea tangle (kombu)-like natural flavor, sea tangle (kombu) extract and/or residue of sea tangle (kombu) extract should be added.

MEANS FOR SOLVING PROBLEMS

As a result of extensive studies in order to solve these problems, we have found that Candida yeast having both aspartate hydroxamate resistance and low temperature sensibility, could provide yeast extracts which contain over a certain content of mannitol, glutamic acid, alanine, 5'-IMP and 5'-GMP. We have also found that the said yeast extract showed strong taste of sea tangle (kombu) and mushrooms-like taste, and have completed the present invention.

An object of the present invention is to provide a composition of yeast extract from genus Candida comprising contents in a dried yeast extract being mannitol above 0.5%, glutamic acid above 2.0%, alanine above 0.5%, 5'-IMP above 1.5% and 5'-GMP above 1.5%.

Another object of the present invention is to provide a yeast from genus Candida resistant to aspartate hydroxamate and taking within 48 hours to grow colonies at 30° C. on a nutrient agar medium, but taking over 96 hours to grow colonies at 15° C.

Further object of the present invention is to provide Candida utilis AHR21 (FERM BP-6099).

A still further object of the present invention is to provide a process for production of a composition of yeast extract comprising culturing said yeast in a medium containing molasses as a main carbon source, isolating the cultured yeast, disrupting the yeast cells and treating the thus obtained destructed cell suspension with enzyme.

The present invention will be explained in detail herein below.

In the yeast extract of the present invention, contents of mannitol, glutamic acid, alanine, 5'-IMP and 5'-GMP are essentially above 0.5%, above 2.0%, above 0.5%, above 1.5% and above 1.5%, respectively. These are preferably above 1.0%, above 3.0%, above 1.0%, above 2.0% and above 2.0%, respectively.

Candida yeast extracts prepared by a conventional enzymatic digestion method have been known to contain glutamic acid, alanine and 5'-1 G. However, the fact that coexistence of over a certain level of glutamic acid, alanine and 5'-1 G with mannitol in Candida yeast can produce sea tangle (kombu)-like or mushroom-like taste, has not been known.

We have found that when the above concentration of each component is simultaneously satisfied, sea tangle (kombu)- like and mushroom-like taste and flavor are felt strongly and with good balance. Namely, addition of nuclease to the yeast which contains mannitol, glutamic acid and alanine may result to enhance taste of glutamic acid with coexisting alanine, 5'-IMP and 5'-GMP, thus to produce sea tangle (kombu)-like taste.

In this invention, a taste means, when the extract is held in the mouth, feelings of full body of the taste or spread of the taste, for example, richness or thickness in taste. A flavor means, when the extract is held in the mouth, feelings of first taste and flavor in the tongue and the nose.

A process for production of a yeast extract of the present invention is explained hereinbelow.

A yeast derived from genus Candida which is resistant to aspartate hydroxamate and takes within 48 hours to grow colonies at 30° C. on a nutrient agar medium, but takes over 96 hours to grow colonies at 15° C., is obtained. A mother strain of the yeast from genus Candida is preferably *Candida tropicalis, Candida lypolitica* and *Candida utilis*. Most preferable strain is *Candida utilis* IFO 0626. These yeasts can be obtained from Institute for Fermentation Osaka, Japan.

(1) [Production of a Strain Resistant to Aspartate Hydroxamate]

Cultured broth of genus Candida is treated by mutagen, such as nitrosoguanidine, UV or X-ray irradiation to produce survival rate of yeast about 0.01–1%. Thus obtained mutant of yeast resistant to aspartate hydroxamate is selected. The yeast strain resistant to aspartate hydroxamate can be selected by the following procedure. The mutant yeast hereinabove is cultured in complete synthetic medium (glucose 1%, ammonium sulfate 0.35%, potassium monophosphate 0.1%, magnesium sulfate 0.05%, sodium chloride 0.05%, calcium chloride 0.05%, and trace metal ions and vitamins), which contains aspartate hydroxamate about 500–1000 μg/ml, then colonies having a diameter of 2-fold larger size than the diameter of the colonies of aspartate hydroxamate sensitive strains (mother strains), are selected. Subsequently, in these aspartate hydroxamate resistant strains, yeast which contains more than 2-fold amount of intercellular alanine (above 0.2% in the yeast extract) than the original strains is selected. The thus obtained alanine and proline accumulated strain is called as AHR3C-2.

② [Collection of Low Temperature Sensitive Strain]

Mutational treatment is performed as same as in the above procedure. Among the obtained mutant yeasts, yeast strains, which takes within 48 hours to grow colonies at 30° C. on a nutrient agar medium, but takes over 96 hours to grow colonies at 15° C., i.e. yeast having low temperature sensitivity, are selected.

Selection of low temperature sensitive yeast is performed as follows.

(1) Mutant aspartate hydroxamate resistant strains are suspended in water. The suspended strain is inoculated in YPD (Yeast Peptone Dextrose) medium and cultured at 30° C. for 18–24 hours.

(2) Cultured yeast is harvested from the cultured medium, and yeast is washed with aseptic water, then the yeast is cultured with MM medium (Bact Yeast Nitrogen Base w/o Amino acid) for 18–24 hours.

(3) Harvested yeast cells are cultured in MM medium with ammonium sulfate at 15° C.

(4) After 6 hours of cultivation, Nystatin is added thereto to 10 μg/ml and the yeast is further cultured at 15° C. for 2 hours.

(5) The thus obtained yeast is harvested from the medium, washed with aseptic water, and reinoculated in YPD medium.

The above procedures (1)–(5) are repeated 2–3 times. The obtained yeast is washed with aseptic water and cultured on YPD agar medium. The strain which takes within 48 hours to grow colonies at 30° C., but takes over 96 hours to grow colonies at 15° C. is selected.

③ [Selection of Strain with High Content of 5'-IMP and 5'-GMP]

The thus obtained yeast is cultured in YPD medium 50 ml at 30° C. for 18 hours. Harvested yeast cells are disrupted by using beads homogenizer. Endoprotease is added to the disrupted cell mixture and treated at 50° C. for 12 hours. Nuclease is further added after the endoprotease treatment and is treated at 65° C. for 3 hours. Deaminase is subsequently added and reacted at 40° C. for 2 hours. The residue in the obtained solution is removed by centrifugation. The supernatant solution is analyzed for sugar, alcohol, amino acids and nucleic acids. From the solution, strains having more than 1.2 fold of contents of 5'-IMP and 5'-GMP comparing to that of mother strain are selected.

Mutant which can be used as yeast material for yeast extract having simultaneously satisfying amounts of mannitol, glutamic acid, alanine, 5'-IMP and 5'-GMP being above 0.5%, 2.0%, 0.5%, 1.5% and 1.5% respectively, can be obtained by the above mentioned method. An example of yeast is *Candida utilis* AHR21. The strain has been deposited in the National Institute of Bioscience and Human-Technology, Agency of Industrial Science and Technology, Ministry of International Trade and Industry, 1-1-3, Higashi, Tsukuba-shi, Ibaraki-ken, Japan, on Sep. 10, 1997, as permanent deposition No. FERM BP-6099.

A process for production of a composition of yeast extract using said mutant yeast is illustrated hereinbelow.

A yeast strain having the properties of the present invention is cultured and is inactivated to prepare a suspension. Examples of carbon sources of culture medium are glucose, saccharide, acetic acid, ethanol, molasses, wood sugar, dextrose corn syrup and sulphite pulp waste liquid. Among them, molasses is preferable in the point that a flavor of substance in the molasses or substances obtained from converted substance in the molasses during fermentation are effective to induce not only sea tangle (kombu)-like taste but also generate sea tangle (kombu)-like flavor.

Examples of nitrogen sources of culture medium are urea, ammonia, ammonium sulfate, ammonium chloride and nitrate. The examples of phosphate, potassium or magnesium sources can be materials which usually are used in industrial purposes. Other components, for example inorganic salts such as zinc, copper, manganese or iron ions; vitamins; amino acids; or nitrogen containing substance such as corn steep liquor can be added. Cultivation temperature may be at 20° C.–38° C., most preferably at 30° C.–36° C., and pH may be pH 3.5–8.0, more preferably at 4.0–6.0.

Cultured yeast is harvested from the medium and washed with water. Washed wet yeast cells and water are mixed as to form ratio from 2:1 to 1:2 by mixing with water to obtain suspension. The said suspension is boiled at 90–110° C. or 20–60 minutes, or spray-dried with inlet temperature at 120–130° C. and outlet temperature at 80–110° C. of the atomizer in the spray drier to prepare dried yeast cells, then the yeast is inactivated.

When the yeast suspension is boiled, inactivated yeast is disrupted by physical means such as homogenizer. When the suspension is applied for spray drying, aqueous suspension of yeast, in which solid parts is set to 10–30%, is prepared. The suspension is treated with enzyme.

Neutral endoprotease is added to the suspension at 100 mg/l, and then treated at 45–55° C. for 6–12 hours.

Subsequently, nuclease is added at 30 mg/l and treated at 60–70° C. for 2–4 hours. Further, deaminase is added at 30 mg/l and treated at 35–45° C. for 1–2 hours.

After enzymatic treatment, residue in the suspension is removed off by centrifugation to the obtained clear solution, If necessary sodium chloride and other materials can be added. Subsequently the mixture is concentrated to desired concentration to obtain the yeast extract. Water content of the yeast extract is preferably 25–35% in the paste product and solid material of the extract is preferably 50–60%.

Following examples illustrate the present invention.

EXAMPLE 1

Obtaining a Mutant Yeast and Production of a Composition of Yeast Extract a. Obtaining a Mutant of Yeast A mother strain *Candida utilis* (IFO 0626) was cultured in the complete synthetic medium (glucose 1%, ammonium sulfate 0.35%, potassium 1-phosphate 0.1%, magnesium sulfate 0.05%, sodium chloride 0.05% calcium chloride 0.05%, trace metal ions and vitamins) at 30° C. for 18 hours. The cultured liquid 10 ml was put on a Petri dish aseptically. The liquid in the Petri dish was directly irradiated with UV-light (15 W, UV lamp) for 60 seconds with maintaining 20 cm distance from the dish, under mixing the liquid with the mixing rod. Comparing to the non-UV irradiated suspension, the rate of viability counts of the yeast in the UV suspension was below 0. 1%.

The irradiated suspension was diluted with aseptic water in order to grow about 100–500 colonies on a Petri dish. The diluted cell suspension was spread on agar plates of the same synthetic medium hereinabove, to which is added with aspartate hydroxamate 1 mg/ml. Simultaneously, the non-UV irradiated cell suspension was spread on agar plate having the same components. These agar plates were aseptically incubated at 30° C. for 48 hours, and the grown colonies, in which a diameter of colonies grown from the UV irradiated cell suspension is 2-fold larger size than a diameter of colonies formed from the UV non-irradiated cell suspension, were selected (hereinafter the selected strain is are referred to as aspartate hydroxamate resistant strain). Yeast extract of the aspartate hydroxamate resistant strain was prepared, and the yeast, the extracted solution of which contained over twice amount of alanine (0.2% in the extracted solution of yeast) as compared with that of the mother strains, was selected. The thus obtained mutant strain is the strain AHR3C-2.

A comparison with concentration of proline, glutamic acid and alanine in the yeast extract of AHR3C-2 strain and the mother strain is shown in Table 1.

TABLE 1

|  | Pro (%) | Glu (%) | Ala (%) |
|---|---|---|---|
| AHR3C-2 | 0.10 | 0.25 | 0.20 |
| IFO 0626 | 0.06 | 0.30 | 0.11 |

*Candida utilis* AHR 21 had the same taxonomical properties with the *Candida utilis* (IFO0626) except for high content of amino acids and nucleic acids.

Resistance to aspartate hydroxamate of the above aspartate hydroxamate resistant yeast (AHR3C-2) and the mother stock *Candida utilis* IFO 0626 is shown in Table 2.

TABLE 2

| Aspartate hydroxamate concentration (μg/ml) | 50 | 100 | 250 | 500 | 1000 |
|---|---|---|---|---|---|
| *Candida utilis* AHR3C-2 | + | + | + | + | + |
| *Candida utilis* IFO 0626 | + | + | + | ± | − |

The thus obtained aspartate hydroxamate resistant strain was irradiated by UV according to the same procedure as above. Subsequently, strains which take within 48 hours to grow colonies at 30° C. on YPD medium, but take over 96 hours to grow colonies at 15° C. were selected. Yeast extract of the thus selected mutant was prepared, then mutants showing content of mannitol, glutamic acid, alanine, 5'-IMP and 5'-GMP is respectively above 0.5%, 2.0%, 0.5%, 1.5%, 1.5%. Among the selected colonies, mutant strains which contain 5'-IMP and 5'-GMP being in excess of above 1.2-fold in yeast extract of AHR3C-2 as dried solid form, was selected and was designated as strain AHR21 which was deposited as FERM BP-6099. *Candida utilis* AHR21 had the same toxonomical properties with the *Candida utilis* (IFO 0626) except for high content of amino acids and nucleic acids.

Concentrations of 5'-IMP and 5'-GMP of the strain AHR21 and the mutant yeast resistant to aspartate hydroxamate (AHR3C-2) in the extract are shown in Table 3 hereinbelow.

TABLE 3

|  | 5' - IMP (%) | 5' - GMP (%) |
|---|---|---|
| AHR21 | 0.15 | 0.10 |
| AHR3C-2 | 0.10 | 0.07 | b. Production of a Composition of Yeast Extract

The strain AHR21 was cultured in a molasses medium (total sugar 8%, phosphate 0.25%, adjusted to pH 5.5 by addition of ammonia) to obtain wet cells (water content 80%).

The wet cells 800 g were washed with water, suspended with aseptic water and were boiled. The boiled yeast suspension was agitated with high pressure homogenizer to disrupt the cells.

Subsequently, obtained mixture was treated with enzyme. Neutral protease (Amano Pharmaceutical Co., Ltd. Protease N) 160 mg was added to the disrupted cell suspension and treated at 50° C. for 12 hours. Nuclease (Amano Pharmaceutical Co., Ltd. Nuclease) 60 mg was added subsequently and treated at 65° C. for 4 hours. Thereafter, deaminase (Amano Pharmaceutical Co., Ltd. Deamizyme) 60 mg was added and treated for 2 hours.

Enzyme treated disrupted cell suspension was centrifuged (10,000 rpm for 10 min.) to obtain the supernatant solution 1260 g. NaCl 24 g was added to the supernatant solution and concentrated by means of using an evaporator to obtain a paste of yeast extract 160 g. A rate of extraction of yeast extract in a solid state for the dried weight of the yeast was 50%. The thus obtained yeast extract is designated as yeast extract (A). Components and content of the obtained yeast extract (A) in solid extract are shown in Table 4 and Table 5.

TABLE 4

Components in the yeast extract (A)

| | |
|---|---|
| extract solid part | 50% |
| NaCl | 15% |
| total nitrogen | 4.5% |
| pH | 6.0 |

TABLE 5

Content of components in extract solid part

| | |
|---|---|
| mannitol | 0.9% |
| glutamic acid | 4.4% |
| alanine | 1.0% |
| 5' - IMP | 2.4% |
| 5' - GMP | 1.8% |

Comparative Example 1

A yeast extract of *Candida utilis* IFO 0626 was prepared according to the same method as in the example 1. The obtained yeast extract is designated as yeast extract (B). Components and content of yeast extract (B) and those in solid extract are shown in Table 6 and Table 7.

TABLE 6

Components in the yeast extract (B)

| | |
|---|---|
| extract solid part | 50% |
| NaCl | 15% |
| total nitrogen | 4.0% |
| pH | 6.0 |

TABLE 7

Content of components in extract solid part

| | |
|---|---|
| mnnitol | 0.8% |
| glutamic acid | 2.6% |
| alanine | 0.7% |
| 5' - IMP | 1.4% |
| 5' - GMP | 1.1% |

Comparative Experiment 1

Sensory evaluation of yeast extracts (A) and (B), each of which is diluted with water of 50° C. to prepare 1% solution, was conducted. The sensory evaluation was performed by two-point discrimination method by 10 expert panelists, who had experience more than 10 years and had undergone training for sensory evaluation. Results are shown in Table 8.

TABLE 8

Sensory evaluation of yeast extracts (A) and (B)

| Items | A is stronger | No difference | B is stronger |
|---|---|---|---|
| Which has the strong sea tangle (kombu) and mushroom-like flavor? | 9 | 1 | 0 |
| Which has good balance of taste, in the whole extract? | 8 | 0 | 2 |

As shown in Table 8, the yeast extract of the present invention has not only significantly superior in sea tangle (kombu) and mushroom-like taste of the (A) with significant difference of 5% but also superior balance of taste in the (A).

EXAMPLE 2

A yeast extract (C) was obtained according to the same method as in example 1 except that AHR-21 obtained in example 1 was cultured in a saccharose medium (saccharose 8%, peptone 1%, yeast extract 0.5% and phosphate 0.25%, adjusted to pH 5.5 by adding ammonium). A component of the obtained yeast extract (C) and amount of content of the component in dried extract are shown in Table 9 and Table 10.

Table 9 Components of Yeast Extract (C)

TABLE 9

Components of yeast extract (C)

| | |
|---|---|
| extract solid part | 50% |
| NaCl | 15% |
| total nitrogen | 4.4% |
| pH | 6.0 |

TABLE 10

Content of components in extract solid part of yeast extract (C)

| | |
|---|---|
| mannitol | 1.2% |
| glutamic acid | 3.5% |
| alanine | 1.0% |
| 5' - IMP | 2.0% |
| 5' - GMP | 1.5% |

Comparative Experiment 2

Sensory evaluation of yeast extracts (A) and (C), each of which is diluted with water of 50° C. to prepare 1% solution, was conducted. The sensory evaluation was performed with two-point discrimination method as same as in the comparative experiment 1. Results are shown in Table 11.

TABLE 11

| Items | A is stronger | No difference | C is stronger |
|---|---|---|---|
| Which has the strong feeling of sea tangle (kombu)-like and mushroom-like flavor ? | 9 | 1 | 0 |

| Items | A is better | No difference | C is better |
|---|---|---|---|
| Whicb has good balance of taste ? | 3 | 5 | 2 |

As shown in Table 11, when the yeast of the present invention was cultured in the molasses medium and the yeast extract was prepared using the said yeast, it was shown that not only taste but also flavor was improved.

Comparative Experiment 3

A noodle soup (A) prepared by using yeast extract (A) obtained in example 1 and a noodle soup (B) prepared by using known sea tangle (kombu) extract were prepared as shown in Table 12.

TABLE 12

| | Noodle soup (A) (%) | Noodle soup (B) (%) |
|---|---|---|
| light soy sauce | 20.0 | 20.0 |
| seasoning sweet sake | 10.0 | 10.0 |
| bonit extract "Ippin" | 20.0 | 20.0 |
| yeast extract (A) | 1.2 | — |
| sea tangle (kombu) extract N-2* | — | 3.0 |
| NaCl | 9.0 | 9.0 |
| "Mitasu" (MSG) | 1.0 | 1.0 |
| water | 36.8 | 35.0 |
| "Extrate" (HAP) | 2.0 | 2.0 |

*product of Asahi Kasei Kogyo K. K.

Sensory evaluation of the noodle soup (A) and (B). each of which is diluted 10-fold with water of 50° C., was carried out with two-point discrimination method by the same 10 panelists as the comparative experiment 1. Results are shown in Table 13.

TABLE 13

| Sensory evaluation between noodle soup (A) and (B) | | | |
|---|---|---|---|
| Items | A is better | No difference | B is better |
| Which has good flavor taste ? | 1 | 9 | 0 |
| Which has richness of flavor ? | 5 | 4 | 1 |

As shown in Table 13, the flavor of the noodle soup prepared by using yeast extract of the present invention was the same as of the noodle soup prepared by using sea tangle (kombu) extract of natural origin, however richness of flavor was superior to the noodle soup prepared by the present invention than the noodle soup prepared by using natural sea tangle (kombu) extract.

EFFECT OF THE INVENTION

The yeast extract of the present invention has almost no yeast flavor with superior to natural sea tangle (kombu)-like and mushroom-like taste. Furthermore, the yeast extract of the present invention has richness as compared to seasonings prepared by extracts of natural sea tangle (kombu) and mushrooms, and has superior balance of taste. When yeast, which is cultured in a medium containing molasses is used, yeast extract with not only taste but also good flavor can be obtained.

Consequently, the present invention can provide preparation of seasonings having sea tangle (kombu)-like and mushroom-like flavor with good taste without adding natural sea tangle (kombu) and natural mushroom components.

What is claimed is:

1. A process for production of a yeast composition which comprises:
   (a) obtaining the yeast of genus Candida which is resistant to aspartate hydroxamate, said yeast being such that the yeast when in an agar medium grows colonies at a temperature of 30° C. in 48 hours, and in 96 hours when the temperature is maintained at 15° C.;
   (b) culturing said yeast in a medium;
   (c) harvesting the cultured yeast;
   (d) disrupting the yeast cells; and
   (e) treating a suspension of disrupted cells with an enzyme selected from the group consisting of endoprotease, nuclease, deaminase, and mixture thereof.

2. A process for production of a yeast composition comprising an extract of yeast of a genus Candida which contains:
   (a) above 0.5% mannitol;
   (b) above 2.0% glutamic acid;
   (c) above 0.5% alanine;
   (d) above 1.5% 5'-IMP; and
   (e) above 1.5% 5'-GMP;
   all of the said %'s being by weight based on the solid content of yeast extract which comprises:
   (a) obtaining the yeast of genus Candida which is resistant to aspartate hydroxamate, said yeast being such that the yeast when in an agar medium grows colonies at a temperature of 30° C. in 48 hours, and in 96 hours when the temperature is maintained at 15° C.;
   (b) culturing said yeast in a medium;
   (c) harvesting the cultured yeast;
   (d) disrupting the yeast cells; and
   (e) treating a suspension of disrupted cells with an enzyme selected from the group consisting of endoprotease, nuclease, deaminase, and mixture thereof.

3. A process for production of a yeast composition which comprises:
   (a) obtaining the yeast of genus Candida which is resistant to aspartate hydroxamate, said yeast being such that the yeast when in an agar medium grows colonies at a temperature of 30° C. in 48 hours, and in 96 hours when the temperature is maintained at 15° C.;
   (b) culturing said yeast in a medium containing molasses as the main carbon source;
   (c) harvesting the cultured yeast;
   (d) disrupting the yeast cells; and
   (e) treating a suspension of disrupted cells with an enzyme selected from the group consisting of endoprotease, nuclease, deaminase, and mixture thereof.

4. A process for production of a yeast composition comprising an extract of yeast of a genus Candida which contains:
   (a) above 0.5% mannitol;
   (b) above 2.0% glutamic acid;
   (c) above 0.5% alanine;
   (d) above 1.5% 5'-IMP; and
   (e) above 1.5% 5'-GMP;
   all of the said %'s being by weight based on the solid content of yeast extract which comprises:
   (a) obtaining the yeast of genus Candida which is resistant to aspartate hydroxamate, said yeast being such that the yeast when in an agar medium grows colonies at a temperature of 30° C. in 48 hours, and in 96 hours when the temperature is maintained at 15° C.;
   (b) culturing said yeast in a medium containing molasses as the main carbon source;
   (c) harvesting the cultured yeast;
   (d) disrupting the yeast cells; and
   (e) treating a suspension of disrupted cells with an enzyme selected from the group consisting of endoprotease, nuclease, deaminase, and mixture thereof.

5. A yeast compostition comprising an extract of yeast of a genus Candida which contains:

(a) above 0.5% mannitol;

(b) above 2.0% glutamic acid;

(c) above 0.5% alanine;

(d) above 1.5% 5'-IMP; and (e) above 1.5% 5'-GMP;

all of the said%'s being by weight based on the solid content of yeast extract.

6. The yeast composition of claim 5, wherein the extract is dried.

7. The yeast composition of claim 5, wherein the yeast is a member selected from the group consisting of *Candida utilis, Candida tropicalis*, and *Candida lypolitica*.

8. The yeast composition according to claim 5, wherein the yeast comprises the genus Candida and is resistant to aspartate hydroxamate, said yeast being such that the yeast when in an agar medium grows colonies at a temperature of 30 ° C. in 48 hours, and in 96 hours when the temperature is maintained at 15 ° C.

9. The yeast composition of claim 5, wherein the yeast is *Candida utilis* AHR21 (FERM BP-6099).

10. The yeast composition of claim 8, wherein the yeast is *Candida utilis* AHR21 (FERM BP-6099).

11. A yeast from genus Candida which is resistant to aspartate hydroxamate and takes within 48 hours to grow colonies at 30° C. on a nutrient agar medium, but takes over 96 hours to grow colonies at 15° C.

12. *Candida utilis* AHR21 (FERM BP-6099).

* * * * *

UNITED STATES PATENT AND TRADEMARK OFFICE
CERTIFICATE OF CORRECTION

PATENT NO.    : 6,344,231 B1
DATED         : February 5, 2002
INVENTOR(S)   : Nakajo et al.

It is certified that error appears in the above-identified patent and that said Letters Patent is hereby corrected as shown below:

<u>Title page,</u>
Item [73], should read as follows: -- Japan Tobacco, Inc., Tokyo, Japan --

Signed and Sealed this

Eighteenth Day of June, 2002

*Attest:*

*Attesting Officer*

JAMES E. ROGAN
*Director of the United States Patent and Trademark Office*